US00PP07924P

United States Patent [19]

Okada et al.

[11] Patent Number: Plant 7,924

[45] Date of Patent: Jul. 28, 1992

[54] CHERRY TREE ROOTSTOCK BIO SIX

[75] Inventors: Makoto Okada, Hagashine; Satomi Saito, Murayama, both of Japan

[73] Assignee: Nakajima Tenkoen Co., Ltd., Higashine, Japan

[21] Appl. No.: 483,857

[22] Filed: Feb. 23, 1990

[51] Int. Cl.[5] ..... A01H 5/00

[52] U.S. Cl. ..... Plt./37

[58] Field of Search ..... Plt./37

*Primary Examiner*—James R. Feyrer

*Attorney, Agent, or Firm*—Armstrong, Nikaido, Marmelstein, Kubovick & Murray

[57] ABSTRACT

A cherry tree rootstock characterized by wide and strong root anchorage, easy vegetative propagation, a thicker shoot and a harder root than the known variety "Colt", a more compact tree shape and darker green leaves than the Colt variety, and a hexaploid (2n=48) chromosome structure as compared to the triploid (2n=24) chromosome structure in the Colt variety.

3 Drawing Sheets

BACKGROUND OF THE INVENTION

This invention is directed to a new variety of cherry tree. The new variety, designated Bio Six, was produced from the known Colt variety and is useful as cherry rootstock.

SUMMARY OF THE INVENTION

The Bio Six cherry tree rootstock variety of this invention is a hexaploid cherry rootstock. Bio Six was developed by treating the Colt cherry rootstock, a known variety, with colchicine in vitro. Bio Six variety is distinguished from the Colt variety by its chromosome number (2n=48) and its leaf, which is dark green with pointed serrations.

DESCRIPTION OF THE INVENTION

Figure 1:
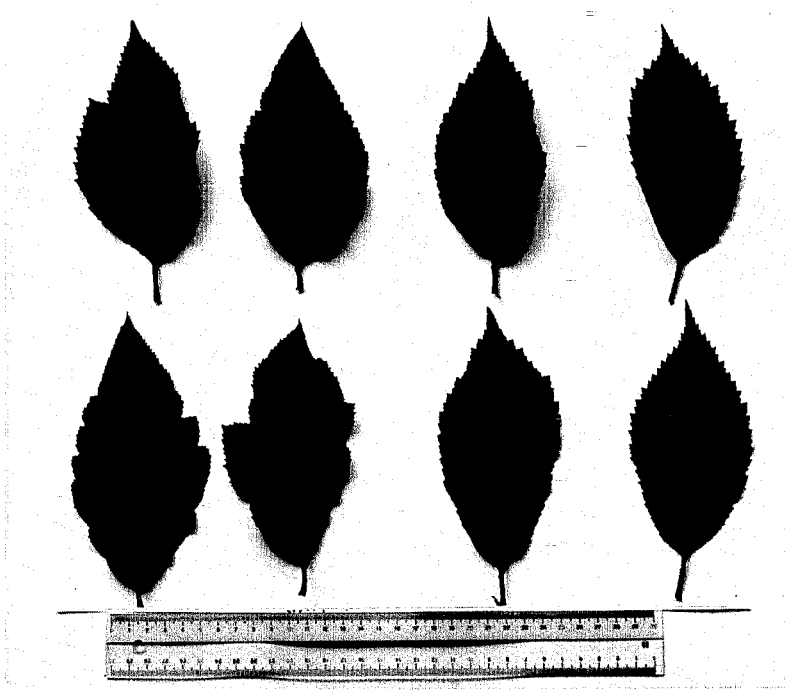
FIG. 1 is a photograph of the leaves Bio Six (left) compared to Colt leaves (right).
Figure 2:
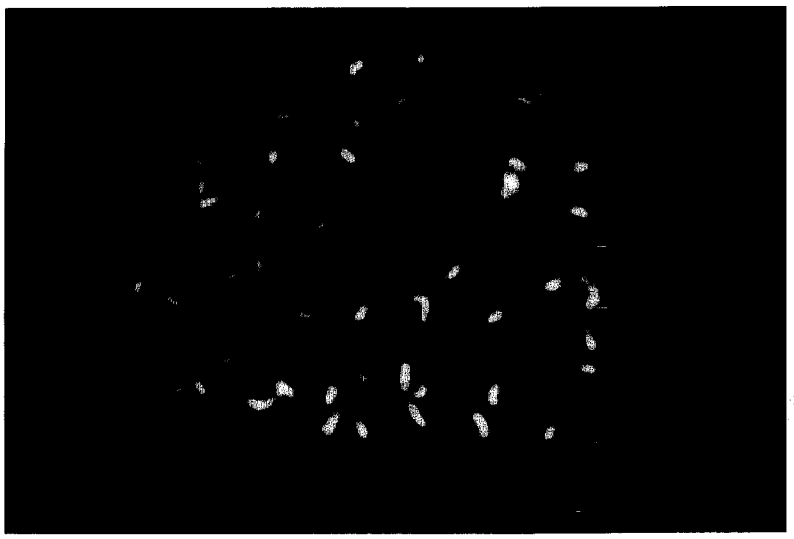
FIG. 2 is a photograph of the chromosomes of Bio Six (2n=48).
Figure 4:
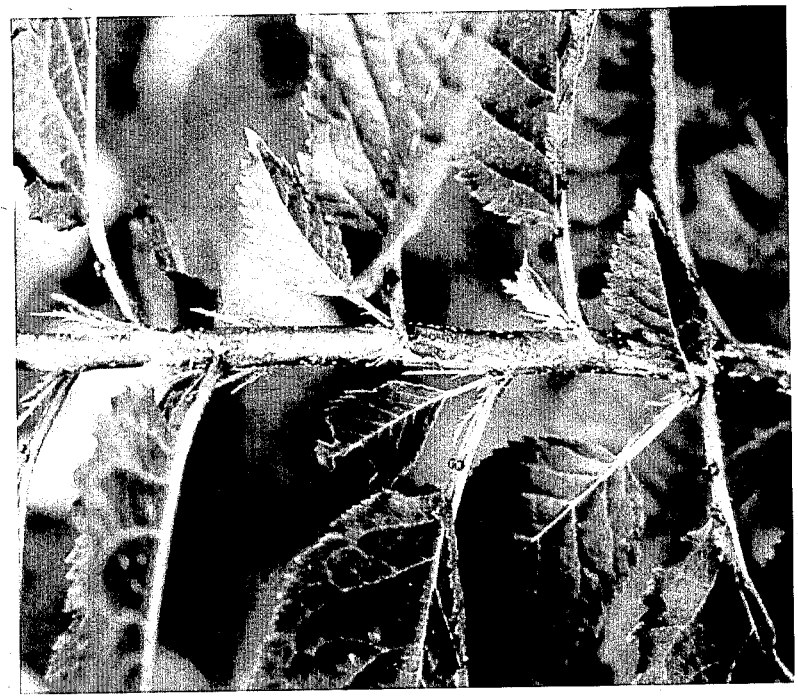
FIG. 4 is a photograph of a one year old Bio Six shoot.
Figure 3:
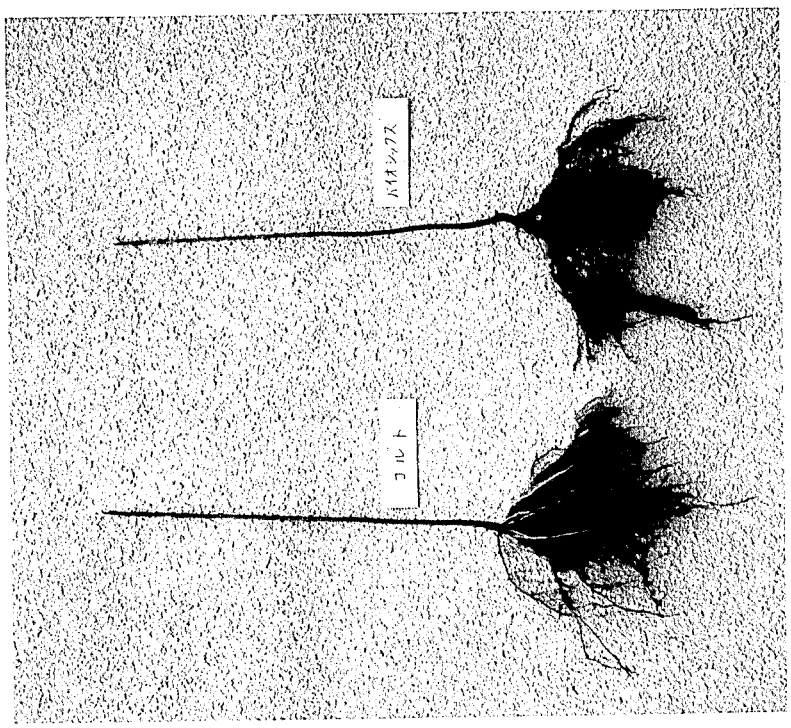
FIG. 3 is a photograph of a root of Bio Six (right) compared to a Colt root (left).
Figure 6:
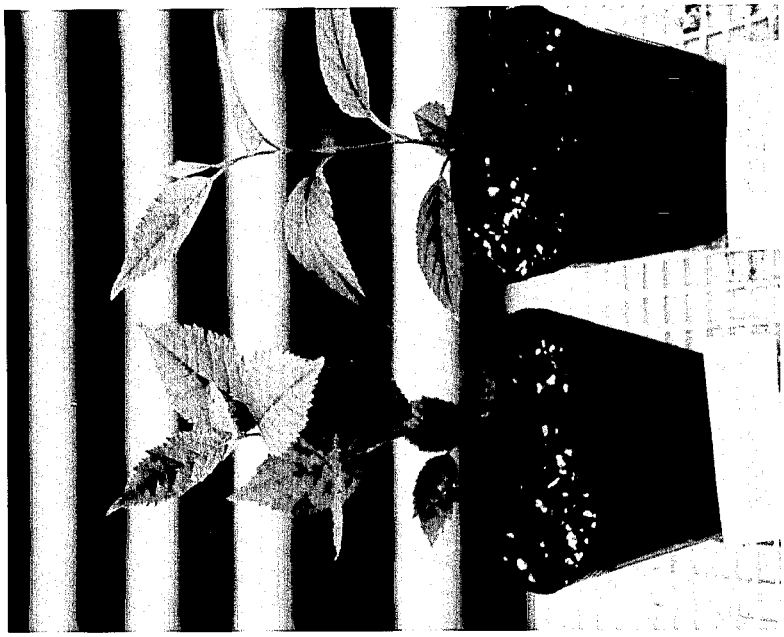
FIG. 6 is a photograph of tissue cultured plant of the Bio Six variety of the invention (left) as compared with the Colt.
Figure 5:
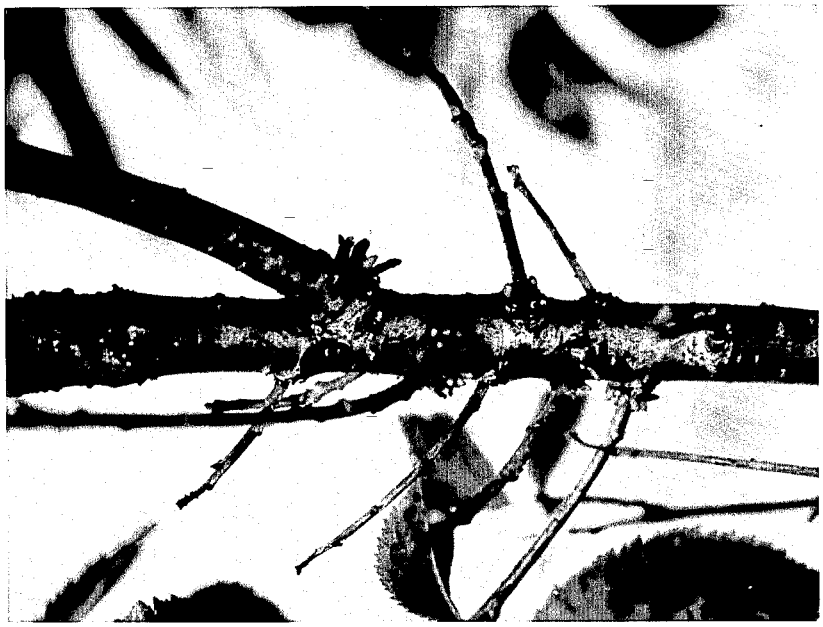
FIG. 5 is a photograph of aerial shoot at base of shoot.

The Bio Six cherry tree rootstock was developed at the Nakajima Tenkoen Research Station, Higashine City, Yamagata prefecture, Japan. In vitro tissue cultured Colt plantlets (*Prunus avium* Lind.) were treated in colchicine. Surviving plantlets were transferred to a new medium. A plantlet, which was distinguished from Colt plantlets in having a thicker shoot and darker green leaves, was selected and planted, giving the Bio Six cherry rootstock variety of the invention. Chromosome analysis indicated that the Bio Six plantlet is hexaploid (2n=48). In contrast, the parent Colt variety is triploid (2n=24). The Bio Six plants obtained by planting in soil were more compact than Colt plants.

DETAILED BOTANICAL DESCRIPTION OF THE INVENTION

The following is a description of the characteristics of the Bio Six cherry tree of this invention.

Tree: The Bio Six tree is compact and smaller than the parent Colt tree. A one year old tree is unfeathered in current growth. Following several years of growth, trees produce preformed roots on the base. Bark is dark reddish brown (Muncell 10R 2.5/4.5) with many grayish waxy areas. Lenticels are small and round with strong brown coloring. Buds are small with a pointed ovoid supported on a medium bud. Buds are slightly held out from axis.

Shoot: Bio Six produces straight and semi upright shoots. Lenticels present on one year old shoots are few in number, small and round with a strong brown color. Color is green with white waxy portion. Internode is shorter than in the Colt parent variety (approximately 1.59 cm in Bio Six, as compared to 2.14 cm in the Colt, in one-year tree).

Leaves: Shape is elliptic. Length is approximately 10.77 cm, width is approximately 5.92 cm, petiole is approximately 2.21 cm. Apex of leaf blade is acuminate. Serration is more pointed than in the Colt leaf. Leaf margin sometimes include irregular serrations. Pubescence of vein under the surface of the leaf is more firm and longer than Colt. One or two leaf grands are present on the petiole, which leaf grands are smaller than Colt, are irregular in size and round to reniform in shape with slight anthocyanin. Petiole is thicker than Colt, with wider grove. Leaf petioles on young trees are with anthocyanin. Stipule is large and feathery in shape. Bio Six leaf is stiffer and thicker than the Colt leaf. Color is dark green (Munsell 5GY $\frac{3}{4}$), which is darker than the Colt leaf color.

Flower: Characteristics of the Bio Six flower have not been confirmed. This characteristic is currently under investigation.

Fruit: The Colt parent is sterile due to its triploidy. Since Bio Six is hexaploid, it may be fertile. This characteristic, however, has not been confirmed and is under current investigation.

Root: Root of Bio Six is harder than Colt root. Anchorage is wide and strong.

Propagation: Asexual reproduction of the invention by tissue culture showed that the described characteristics and distinctions are faithfully reproduced and are transmitted through succeeding propagation.

Suckering: Bio Six produces few suckers.

Hardiness: No injury of Bio Six due to freezing has been observed.

Use: Bio Six is useful for rootstock of sweet cherry variety.

Graft compatibility: Bio Six has been shown to be compatible with all sweet cherry varieties tested so far.

Influence on scion varieties: Insufficient data currently exists with respect to the influence of Bio Six to scion varieties as compared with Colt and other cherry rootstock varieties. Such characteristics are currently being investigated.

We claim:

1. A new and distinct variety of cherry tree rootstock, substantially as illustrated and described herein, particularly characterized by a thicker shoot and darker green leaves than the known variety "Colt", a more compact tree shape than the Colt variety, and a hexaploid (2n=48) chromosome structure as compared to the triploid (2n=24) chromosome structure in the Colt variety.

* * * * *